US012586670B2

(12) United States Patent
Castle et al.

(10) Patent No.: US 12,586,670 B2
(45) Date of Patent: Mar. 24, 2026

(54) SYSTEM AND METHOD FOR FAST MONTE CARLO DOSE CALCULATION USING A VIRTUAL SOURCE MODEL

(71) Applicants: James Castle, Lexington, KY (US); Quan Chen, Lexington, KY (US); Xue Feng, Lexington, KY (US)

(72) Inventors: James Castle, Lexington, KY (US); Quan Chen, Lexington, KY (US); Xue Feng, Lexington, KY (US)

( * ) Notice: Subject to any disclaimer, the term of this patent is extended or adjusted under 35 U.S.C. 154(b) by 1163 days.

(21) Appl. No.: 17/528,590

(22) Filed: Nov. 17, 2021

(65) Prior Publication Data

US 2023/0154586 A1     May 18, 2023

(51) Int. Cl.
|  |  |
|---|---|
| *G16H 20/10* | (2018.01) |
| *G06T 7/00* | (2017.01) |

(Continued)

(52) U.S. Cl.
CPC .......... *G16H 20/10* (2018.01); *G06T 7/0012* (2013.01); *G16H 15/00* (2018.01); *G16H 30/40* (2018.01);

(Continued)

(58) Field of Classification Search
CPC ........ G16H 20/10; G16H 15/00; G16H 30/40; G16H 50/50; G16H 20/40; G06T 7/0012;

(Continued)

(56) References Cited

U.S. PATENT DOCUMENTS

| | | | |
|---|---|---|---|
| 6,714,620 B2 * | 3/2004 | Caflisch | A61N 5/103 |
| | | | 378/65 |
| 11,872,764 B2 * | 1/2024 | Rajapakse | G06T 7/11 |

(Continued)

Primary Examiner — Ryan J. Walters

(57) ABSTRACT

The present disclosure relates to a method and apparatus for fast Monte Carlo (MC) dose calculation using a virtual source model (VSM). The method includes: receiving three-dimensional (3D) CT images obtained by a CT system; receiving 3D planned dose images, 3D organ segmentation contour images, and radiotherapy plans generated by a treatment planning system (TPS); processing 3D CT images, 3D planned dose images, 3D organ segmentation contour images to have the same spatial resolution and matrix size; further processing 3D CT images to convert image intensity to 3D density maps; processing the radiotherapy plans to generate instructions on how to simulate plan delivery; building VSM using inverse cumulative density function (CDF) tables for the simulation of radiotherapy plans, wherein the step of building VSM comprises: receiving output data files containing phase-space information for the radiation output of a specific medical linear accelerator treatment head; calculating the probability of the inplane and crossplane positions of the radiation particles reverse trans-ported from the phase-space surface back to the treatment head; calculating the Gaussian means and standard devia-tions of the radiation particles' positions at the treatment head; calculating the probabilities for the source of each radiation particle; calculating the probabilities for the medi-cal linear accelerator treatment head to produce different radiation particle species; binning the inplane position prob-ability information of radiation particles into a single his-togram for each source and radiation particle species; bin-ning the crossplane position probability information of radiation particles into histograms for each bin of the inplane position histogram for each source and radiation particle species; binning the inplane direction cosine probability information of radiation particles into histograms for each bin of the inplane position histogram for each source and radiation particle species; binning the crossplane direction cosine probability information of radiation particles into histograms for each bin of the crossplane position histogram for each source and radiation particle species; binning the kinetic energy probability information of radiation particles into radially binned histograms for each source and radiation (Continued)

100 particle species; converting probability densities for inplane and crossplane positions, inplane and crossplane direction cosines, and kinetic energies histograms into cumulative probability densities for each source and radiation particle species; and inverting cumulative probability densities and converting into probability binned inverse CDF tables; simulating and transporting external beams using VSM through virtual treatment machines to the 3D density maps according to radiotherapy plans to produce 3D simulated dose images; and post-processing the 3D planned dose images, 3D organ segmentation contour images, and the 3D simulated dose images to obtain a final report comparing planned versus simulated dose images.

19 Claims, 8 Drawing Sheets

(51) Int. Cl.
    *G16H 15/00*        (2018.01)
    *G16H 30/40*        (2018.01)
    *G16H 50/50*        (2018.01)

(52) U.S. Cl.
    CPC ...  *G16H 50/50* (2018.01); *G06T 2207/10081*
                                        (2013.01)

(58) Field of Classification Search
    CPC ........ G06T 2207/10081; A61N 5/1071; A61N
                                       2005/1034
    See application file for complete search history.

(56)                     References Cited

U.S. PATENT DOCUMENTS

| 2007/0282575 A1* | 12/2007 | Gossage | ................. | G06F 30/20 |
| | | | | 703/2 |
| 2015/0154374 A1* | 6/2015 | Hissoiny | ................ | G16H 50/30 |
| | | | | 703/6 |
| 2022/0161062 A1* | 5/2022 | Adamson | .............. | G16H 40/63 |
| 2024/0366962 A1* | 11/2024 | Sjolund | .................. | G16H 50/70 |

* cited by examiner

SYSTEM AND METHOD FOR FAST MONTE CARLO DOSE CALCULATION USING A VIRTUAL SOURCE MODEL

STATEMENT OF GOVERNMENT INTEREST

This invention was made with government support under Grant No. R44CA254844 awarded by The National Institute of Health. The government has certain rights in the invention.

CROSS-REFERENCE TO RELATED APPLICATION

Not applicable.

FIELD

This disclosure relates to computed tomography (CT) operations that develop and validate a system for fast Monte Carlo Dose calculation using a virtual source model.

BACKGROUND

Monte Carlo (MC) simulation is regarded as the gold standard for estimating the amount of energy deposited into a medium by ionizing radiation. The clinical utility of using MC simulations for independent dose calculations is often hindered by the computational resources and time required to run these simulations. Often, MC simulations begin with phase space files (PSF), which are derived from full simulations of primary electron interactions within the treatment head and store the resulting particles at a reference surface a set distance from the treatment head. Given an accurate representation of the geometries of the treatment head, PSF will contain the most accurate description of the resulting beam. Monte Carlo dose calculations must be run with a large number of simulated particles to achieve clinically acceptable accuracy. This, in turn, requires input PSF that contain a large (~billions), but finite, number of particles that take up significant amounts of disk space to store (~GB). A major bottleneck in MC calculations arises from the input/output (I/O) time required for reading large PSF from the disk. Hard disk drives (HDDs) have buffered file read rates up to ~150 MB/s, while solid state drives (SSDs) have buffered file read rates up to ~500 MB/s. Even with the increased read rate for an SSD, a best-case scenario for reading a 50 GB PSF will take ~100 s just to load the file. This I/O burden becomes more significant with methods that use multi-core processing, as the multiple processes will compete over the same I/O bandwidth. A common solution to ease the I/O burden is to develop so-called virtual source models (VSM), which approximate the behavior of particles at the PSF surface. Virtual source models have two distinct advantages: they take up significantly less disk space and allow for infinite sampling. Particle parameters from the PSF must be modeled precisely for the VSM to yield quality simulations.

SUMMARY

Examples of the present disclosure provide a method for fast Monte Carlo dose calculation using a VSM.

According to a first aspect of the present disclosure, a computer-implemented method for fast MC dose calculation using a VSM. The method may include receiving three-dimensional (3D) CT images obtained by a CT system; receiving 3D planned dose images, 3D organ segmentation contour images, and radiotherapy plans generated by a treatment planning system (TPS); processing 3D CT images, 3D planned dose images, 3D organ segmentation contour images to have the same spatial resolution and matrix size; further processing 3D CT images to convert image intensity to 3D density maps; processing the radiotherapy plans to generate instructions on how to simulate plan delivery; building VSM using inverse cumulative density function (CDF) tables for the simulation of radiotherapy plans, wherein the step of building VSM comprises: receiving output data files containing phase-space information for the radiation output of a specific medical linear accelerator treatment head; calculating the probability of the inplane and crossplane positions of the radiation particles reverse transported from the phase-space surface back to the treatment head; calculating the Gaussian means and standard deviations of the radiation particles' positions at the treatment head; calculating the probabilities for the source of each radiation particle; calculating the probabilities for the medical linear accelerator treatment head to produce different radiation particle species; binning the inplane position probability information of radiation particles into a single histogram for each source and radiation particle species; binning the crossplane position probability information of radiation particles into histograms for each bin of the inplane position histogram for each source and radiation particle species; binning the inplane direction cosine probability information of radiation particles into histograms for each bin of the inplane position histogram for each source and radiation particle species; binning the crossplane direction cosine probability information of radiation particles into histograms for each bin of the crossplane position histogram for each source and radiation particle species; binning the kinetic energy probability information of radiation particles into radially binned histograms for each source and radiation particle species; converting probability densities for inplane and crossplane positions, inplane and crossplane direction cosines, and kinetic energies histograms into cumulative probability densities for each source and radiation particle species; and inverting cumulative probability densities and converting into probability binned inverse CDF tables; simulating and transporting external beams using VSM through virtual treatment machines to the 3D density maps according to radiotherapy plans to produce 3D simulated dose images; and post-processing the 3D planned dose images, 3D organ segmentation contour images, and the 3D simulated dose images to obtain a final report comparing planned versus simulated dose images.

According to a second aspect of the present disclosure, an apparatus for fast MC dose calculation using a VSM. The apparatus may include one or more processors, a display, and a non-transitory computer-readable memory storing instructions executable by the one or more processors. Wherein the instructions are configured to receive three-dimensional (3D) CT images obtained by a CT system; receive 3D planned dose images, 3D organ segmentation contour images, and radiotherapy plans generated by a treatment planning system (TPS); process 3D CT images, 3D planned dose images, 3D organ segmentation contour images to have the same spatial resolution and matrix size; further process 3D CT images to convert image intensity to 3D density maps; process the radiotherapy plans to generate instructions on how to simulate plan delivery; build VSM using inverse cumulative density function (CDF) tables for the simulation of radiotherapy plans, wherein the step of building VSM includes instructions that are configured to:

receive output data files containing phase-space information for the radiation output of a specific medical linear accelerator treatment head; calculate the probability of the inplane and crossplane positions of the radiation particles reverse transported from the phase-space surface back to the treatment head; calculate the Gaussian means and standard deviations of the radiation particles' positions at the treatment head; calculate the probabilities for the source of each radiation particle; calculate the probabilities for the medical linear accelerator treatment head to produce different radiation particle species; bin the inplane position probability information of radiation particles into a single histogram for each source and radiation particle species; bin the crossplane position probability information of radiation particles into histograms for each bin of the inplane position histogram for each source and radiation particle species; bin the inplane direction cosine probability information of radiation particles into histograms for each bin of the inplane position histogram for each source and radiation particle species; bin the crossplane direction cosine probability information of radiation particles into histograms for each bin of the crossplane position histogram for each source and radiation particle species; bin the kinetic energy probability information of radiation particles into radially binned histograms for each source and radiation particle species; convert probability densities for inplane and crossplane positions, inplane and crossplane direction cosines, and kinetic energies histograms into cumulative probability densities for each source and radiation particle species; and invert cumulative probability densities and convert into probability binned inverse CDF tables; simulate and transport external beams using VSM through virtual treatment machines to the 3D density maps according to radiotherapy plans to produce 3D simulated dose images; and post-process the 3D planned dose images, 3D organ segmentation contour images, and the 3D simulated dose images to obtain a final report comparing planned versus simulated dose images.

According to a third aspect of an example of the present disclosure, a non-transitory computer-readable storage medium having stored therein instructions is provided. When the instructions are executed by one or more processors, the instructions cause the apparatus to perform acts comprising receiving three-dimensional (3D) CT images obtained by a CT system; receiving 3D planned dose images, 3D organ segmentation contour images, and radiotherapy plans generated by a treatment planning system (TPS); processing 3D CT images, 3D planned dose images, 3D organ segmentation contour images to have the same spatial resolution and matrix size; further processing 3D CT images to convert image intensity to 3D density maps; processing the radiotherapy plans to generate instructions on how to simulate plan delivery; building VSM using inverse cumulative density function (CDF) tables for the simulation of radiotherapy plans, wherein the step of building VSM comprises: receiving output data files containing phase-space information for the radiation output of a specific medical linear accelerator treatment head; calculating the probability of the inplane and crossplane positions of the radiation particles reverse transported from the phase-space surface back to the treatment head; calculating the Gaussian means and standard deviations of the radiation particles' positions at the treatment head; calculating the probabilities for the source of each radiation particle; calculating the probabilities for the medical linear accelerator treatment head to produce different radiation particle species; binning the inplane position probability information of radiation particles into a single histogram for each source and radiation particle species; binning the crossplane position probability information of radiation particles into histograms for each bin of the inplane position histogram for each source and radiation particle species; binning the inplane direction cosine probability information of radiation particles into histograms for each bin of the inplane position histogram for each source and radiation particle species; binning the crossplane direction cosine probability information of radiation particles into histograms for each bin of the crossplane position histogram for each source and radiation particle species; binning the kinetic energy probability information of radiation particles into radially binned histograms for each source and radiation particle species; converting probability densities for inplane and crossplane positions, inplane and crossplane direction cosines, and kinetic energies histograms into cumulative probability densities for each source and radiation particle species; and inverting cumulative probability densities and converting into probability binned inverse CDF tables; simulating and transporting external beams using VSM through virtual treatment machines to the 3D density maps according to radiotherapy plans to produce 3D simulated dose images; and post-processing the 3D planned dose images, 3D organ segmentation contour images, and the 3D simulated dose images to obtain a final report comparing planned versus simulated dose images.

Other aspects and features according to the example embodiments of the disclosed technology will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

DETAILED DESCRIPTION

Reference will now be made in detail to example embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the disclosure. Instead, they are merely examples of apparatuses and methods consistent with aspects related to the disclosure as recited in the appended claims.

The terminology used in the present disclosure is for the purpose of describing particular embodiments only and is not intended to limit the present disclosure. As used in the present disclosure and the appended claims, the singular forms "a," "an," and "the" are intended to include the plural forms as well, unless the context clearly indicates otherwise. It shall also be understood that the term "and/or" used herein is intended to signify and include any or all possible combinations of one or more of the associated listed items.

It shall be understood that, although the terms "first," "second," "third," etc. may be used herein to describe various information, the information should not be limited by these terms. These terms are only used to distinguish one category of information from another. For example, without departing from the scope of the present disclosure, first information may be termed as second information; and similarly, second information may also be termed as first information. As used herein, the term "if" may be understood to mean "when" or "upon" or "in response to a judgment" depending on the context.

The present disclosure related to an algorithm for fast MC dose calculation using a VSM for Varian→Linac. The disclosure is not limited to this treatment delivery machine and can be easily extended to other machines.

Figure 1:
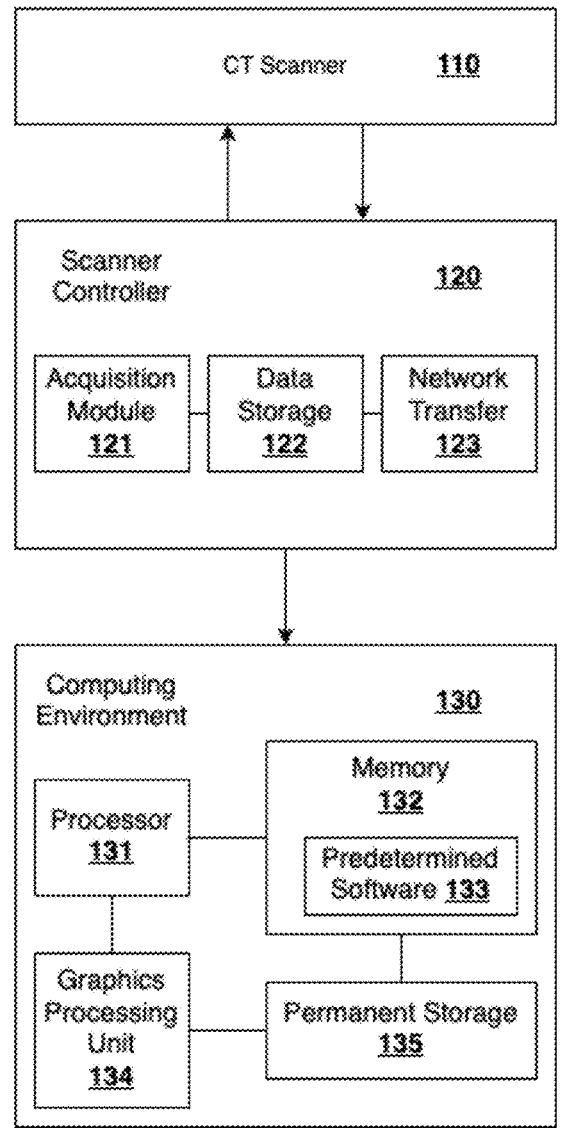
FIG. 1 is a system diagram of CT scanner, controller, and computing environment illustrating an operating environment capable of implementing aspects of the present disclosure.

FIG. 1 shows a system diagram of CT scanner 110, controller 120 and computing environment 130. The CT scanner 110 is used to obtain CT images covering any region of a subject and is controlled by the scanner controller 120. The scanner controller 120 contains the acquisition module 121 that drives the CT scanner 110, the data storage module 122 that stores the CT images of different subjects, and the network transfer module 123 that sends the CT images to another computing environment 130. The computing environment 130 contains processor 131, graphics processing unit (GPU) 134, memory 132, and permanent storage 135 to perform given directions. In executing the directions, the predetermined software 133 is loaded into memory 132 and executed by processor 131 to yield the desired output.

The processing component 120 typically controls overall operations of the computing environment 130, such as the operations associated with display, data acquisition, data communications, image processing, and MC dose calculation. The processor 131 may include one or more processors to execute instructions to perform all or some of the steps in the above-described methods. Moreover, the processor 131 may include one or more modules which facilitate the interaction between the processor 131 and other components. The processor may be a Central Processing Unit (CPU), a microprocessor, a single chip machine, a GPU, or the like. GPU 134 can include one or more GPUs interconnected to execute one or more GPU executable programs.

The memory 132 is configured to store various types of data to support the operation of the computing environment 130. Examples of such data comprise instructions for any applications or methods operated on the computing environment 130, CT datasets, image data, etc. The memory 132 may be implemented by using any type of volatile or non-volatile memory devices, or a combination thereof, such as a static random-access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic or optical disk.

In an embodiment, the computing environment 130 may be implemented with one or more application specific integrated circuits (ASICs), digital signal processors (DSPs), digital signal processing devices (DSPDs), programmable logic devices (PLDs), field programmable gate arrays (FPGAs), GPUs, controllers, micro-controllers, microprocessors, or other electronic components, for performing the above methods.

The fast MC dose calculation using a VSM is programmed as one set of predetermined software 133 and installed on the computing environment 130. When the computing environment 130 receives CT images from scanner controller 120, and generates a treatment plan, planned dose, and image segmentations for a patient, the predetermined software 133 is executed to generate MC dose calculation results.

Figure 2:
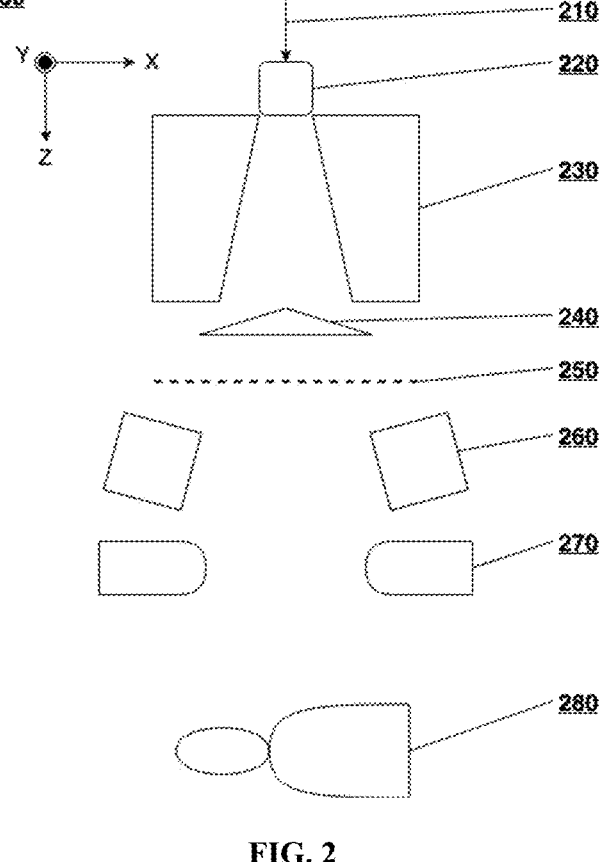
FIG. 2 is a schematic illustrating a treatment head for a medical linear accelerator related to aspects of the present disclosure.

FIG. 2 shows a schematic illustrating an example treatment head for a medical linear accelerator related to aspects of the present disclosure. Electrons beams 210 are accelerated to high energies and directed at the tungsten target 220. Bremsstrahlung interactions within the tungsten target create a shower of particles called a treatment beam. Primary collimators 230 are used to focus the treatment beam and particles that have been scattered at large angles. Fattening filter 240 may or may not be used to flatten the fluence of the particle shower. Phase space files resulting from simulation of electron interactions in the treatment head 220 will contain particles transported to a phase-space surface 250 that is located past the primary collimators 230 and flattening filter 240. Moveable jaws 260 and multi-leaf collimator (MLC) leaves 270 are used to collimate the treatment beam further to fit the treatment plan. Treatment beams that have not been blocked will then deliver doses to the patient 280. The disclosure is not limited to this specific treatment head and can be easily extended to other treatment heads.

Figure 3:
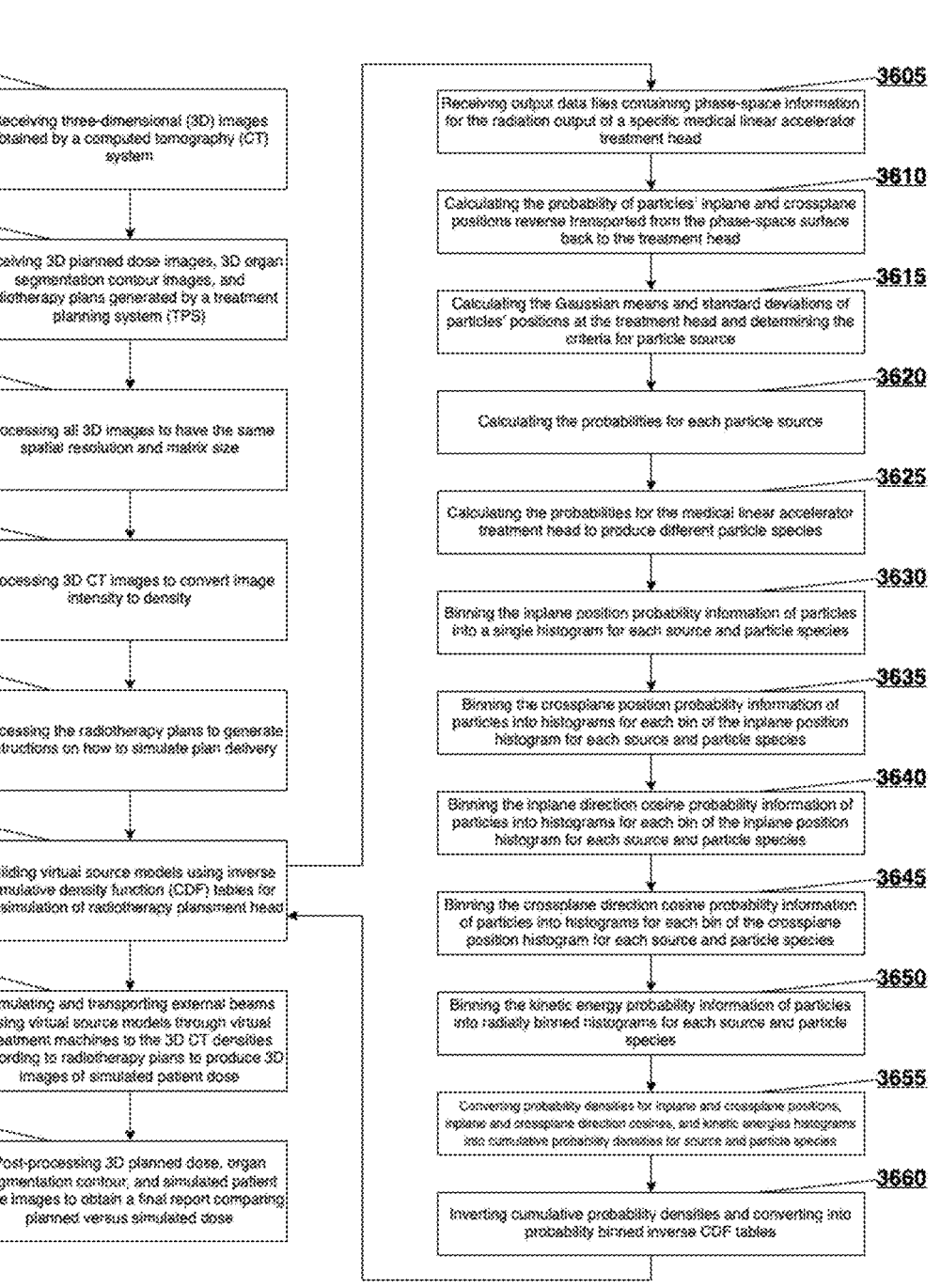
FIG. 3 is a flow chart illustrating a method for fast MC dose calculation using a VSM, according to an example of the present disclosure.

FIG. 3 shows an example flow chart setting forth the steps of a method 3000 in accordance with the present disclosure.

In step 3100, 3D CT images are received.

In step 3200 3D planned dose images, 3D segmentation contour images, and radiotherapy treatment plans generated by a TPS are received.

In step 3300, all 3D images are processed to have the same spatial resolution and matrix size.

CT imaging protocols including pixel spacing, axial slice thickness, and field-of-view in the z-direction can vary from different scans. Further, TPS-generated doses and contours can use different pixel spacing, axial slice thickness, and field-of-view when generating treatment plans. Therefore, to create uniform spatial resolution and matrix size across all 3D images, the input CT images were all uniformly resampled to have axial in-plane resolution of $0.9756 \times 0.9756$ mm$^2$ and 3 mm slice-thickness. The in-plane matrix size was fixed to $512 \times 512$ so that the corresponding field-of-view was $500 \times 500$ mm$^2$. All other images were resampled to match the CT matrix size and field of view by either zero-padding or center-cropping in the axial plane after resampling. The resulting image matrix size was $512 \times 512 \times$ N, in which N is the number of slices after resampling.

To normalize the image intensity, the voxel values outside of $-1000$ to 600 Hounsfield unit (HU) were set to $-1000$ and 600, respectively.

In step 3400 3D image HU voxels are converted to densities using an intensity value to density table (IVDT). Intensity value to density tables contain multiple HU values and the density in g/cm$^3$ to which they correspond. Linear interpolation is used between HU values to convert all voxels to densities.

In step 3500 radiotherapy plans are parsed and converted to a set of instructions on how to simulate plan delivery.

Radiotherapy plans output from a TPS are usually in the DICOM format and split plans into a number of treatment beams and treatment beam control points. Each treatment beam will have an energy mode, total number of monitor units (MU), and number of control points. Each control point is machine specific and may contain information on control point MU, source-axis distance, machine isocenter position, gantry rotation, couch rotation, collimator rotation, jaw positions, and MLC leaf positions. All fields are extracted from the DICOM file and put into a plain text file that will be read from the MC algorithm to simulate the treatment plan.

In step 3600 VSM are built using inverse cumulative density function (CDF) tables for the simulation if radiotherapy plans. Each VSM need only be built once, and the use of these models is the key source of computation speed in MC calculations. Steps 3605-3665 show in detail how each VSM are built.

In step 3605 PSF containing phase-space information for the radiation output of a specific medical linear accelerator treatment head are received.

The International Atomic Energy Agency (IAEA) created a standard for the design of PSF, wherein each particle stored within will have information on its species, inplane (X) and crossplane (Y) positions, inplane (U) and crossplane (V) direction cosines, and kinetic energy (E). Each particle is set at the same Z distance from the treatment head and has the same Z-direction cosine (W) value of 1. Particle species include photons, electrons, and positrons, >99% of which are photons.

In step 3610 the PSF are parsed and the probabilities of particles' inplane and crossplane positions reverse transported from the phase-space surface back to the treatment head are calculated.

PSF do not contain information particle origin, and not all particles created in the treatment head come from the same source. Most photons arise from Bremsstrahlung interactions within the treatment head, but a fraction will be scattered by the primary collimators and/or flattening filter and still make it to the phase-space surface. To determine photon origin, the inplane and crossplane positions of photons are reverse transported back to from the phase-space surface to the treatment head and histograms are used to calculate the probabilities of photon inplane and crossplane positions.

In step 3615 the Gaussian means and standard deviations of particles' positions at the treatment head are used to determine the criteria for particle source.

Figure 4:
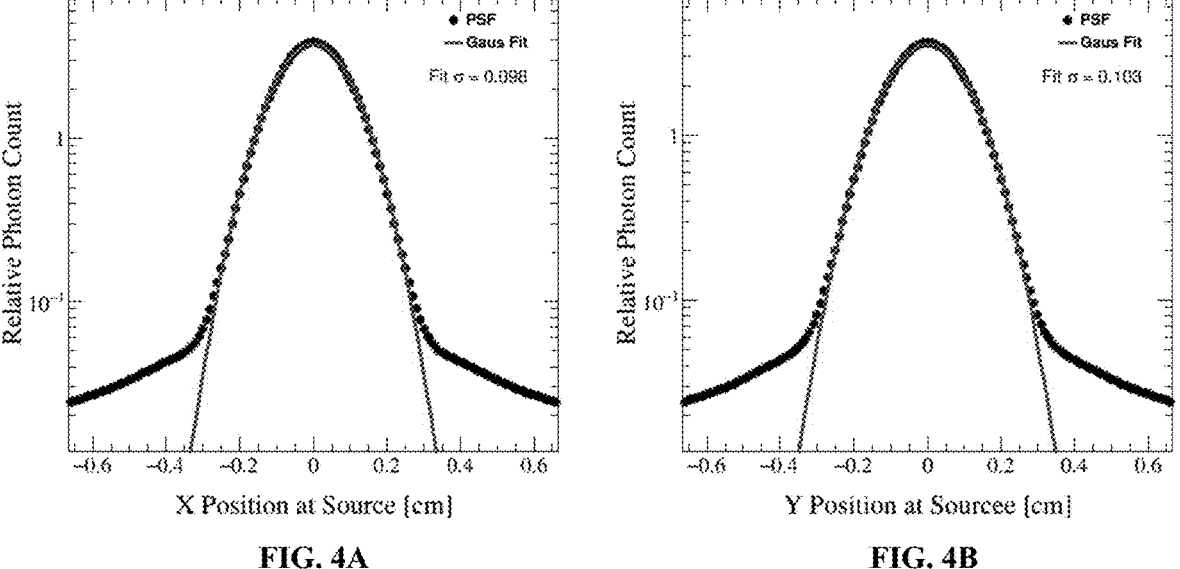
FIG. 4A depicts the Gaussian fits to the probability density for photon inplane position reverse transported to the treatment head, according to an example of the present disclosure.
FIG. 4B depicts the Gaussian fits to the probability density for photon crossplane position reverse transported to the treatment head, according to an example of the present disclosure.

The electron beam focus on the tungsten is Gaussian in shape, so the primary photon positions should follow the same shape. Gaussian fits are performed to photon inplane and crossplane positions at the treatment head, as illustrated in FIG. 4. If a photon's position is within three standard deviations of the Gaussian mean, then a photon is considered a primary photon. All other photons are considered scattered photons. Electrons and positions are considered as purely scattered and grouped together to reduce noise.

In step 3620 the probabilities of each particle source are calculated.

In step 3625 the probabilities of each particle species are calculated.

In step 3630 the probabilities of particle inplane position are binned into a histogram for each particle species and source.

The inplane positions for each particle are counted separately for primary photons, scattered photons, and electrons/positrons. Histograms for photons use a bin width of 0.1 cm, while the electron/positron histograms have a bin width of 0.2 cm to reduce noise.

In step 3635 the probabilities of particle crossplane position are binned into histograms for each bin of the inplane position histogram, particle species, and source.

The crossplane positions of each particle are counted in histograms using the exact grouping and binning as particle inplane positions. Further, crossplane position histograms are generated for every inplane position bin to preserve the correlation between particle inplane and crossplane position.

In step 3640 the probabilities of particle inplane direction cosines are binned into histograms for each bin of the inplane position histogram, particle species, and source.

In step 3645 the probabilities of particle crossplane direction cosines are binned into histograms for each bin of the crossplane position histogram, particle species, and source.

Instead of counting inplane and crossplane direction cosine values directly, the quantities U'-U and V'-V, where U'≡X/Z and V'≡Y/Z are counted. The rationale was that most particles direction will, on average follow their geometric position with respect to the origin at the treatment head with some fluctuations around that vector. This is indeed relevant for primary photons, where such histograms show a peak around 0 with very small Gaussian spread. The relationship is less relevant for scattered photons and electrons/positrons, as the scattering processes do not preserve information on particle origin. Histograms for direction cosine difference use a bin width of 0.0005 to capture the small fluctuation behavior, while the electron/positron histograms use a bin width of 0.02 to reduce noise. Further, U'-U histograms are generated for every inplane position bin and V'-V histograms were generated for every crossplane position bin, as fluctuation size is related to distance from the origin.

In step 3650 the probabilities of particle kinetic energy are binned into radially binned histograms for each particle species and source.

Histograms for photons use a bin width of 0.02 MeV, while the electron/positron histogram have a bin width of 0.05 MeV to reduce noise. Further, separate kinetic energy histograms were counted based on radial position. A kinetic energy histogram was generated every 0.5 cm in $R = \sqrt{X^2 + Y^2}$ up to R=5.5 cm. Particles with R>5.5 cm are counted in a single histogram.

In step 3655 probability densities are converted into cumulative probability densities for particle inplane and crossplane directions, inplane and crossplane direction cosines, and kinetic energies for each source and particle species.

In step 3660 the cumulative probabilities are converted into probability binned inverse CDF tables.

Inverse CDFs are stored as binary files containing floating-point precision lookup tables. Inverse CDF tables are structured such that the first column represents probability and values range from 0 to 1 using a step 0.00005. The second column contains the inverted CDF for a certain value. For example, it may contain the primary photon inplane position. Inverse CDF tables are used in conjunction with sampling a random uniform number. Here, a random uniform number is sampled, found in the lookup table, and linear interpolation is used to find the primary photon inplane position corresponding to said sampled random number.

Figures 5, 5A, 5B:
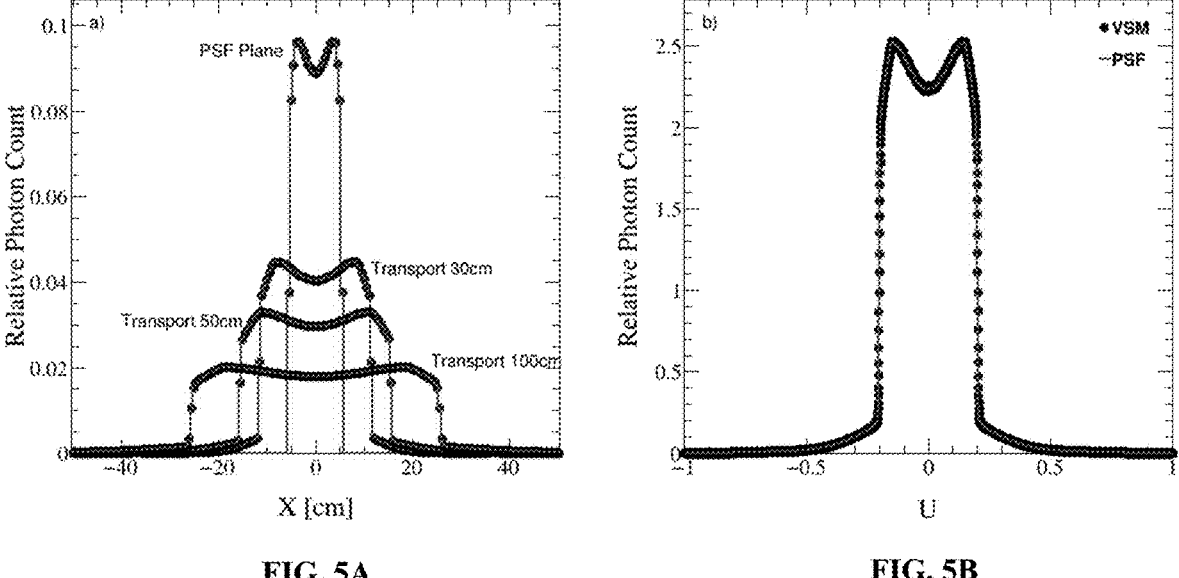
FIG. 5A shows VSM-sampled and PSF-read particle inplane position distributions transported from the PSF plane to the treatment isocenter for a 6 MV treatment beam without a flattening filter, according to an example of the present disclosure.
FIG. 5B shows VSM-sampled and PSF-read particle inplane direction cosine distributions for a 6 MV treatment beam without a flattening filter, according to an example of the present disclosure.
Figure 6:
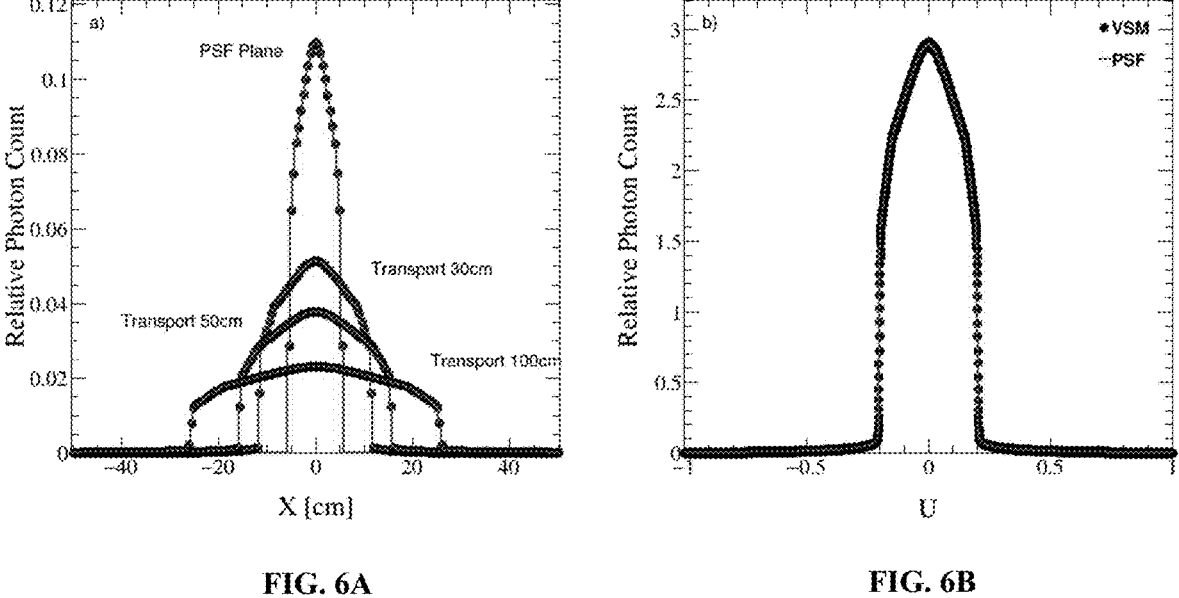
FIG. 6A shows VSM-sampled and PSF-read particle inplane position distributions transported from the PSF plane to the treatment isocenter for a 6 MV treatment beam with a flattening filter, according to an example of the present disclosure.
FIG. 6B shows VSM-sampled and PSF-read particle inplane direction cosine distributions for a 6 MV treatment beam with a flattening filter, according to an example of the present disclosure.

The VSM were first validated by simulating 100 million particles and using a $\chi^2$ test to compare the particle distributions at the phase-space surface (Z=26.7 cm) and isocenter (Z=100 cm) from the VSM to the particle distributions read directly from the PSF at the same locations. These tests were run to verify the quality of the simulated particles for 6 MV and 10 MV beam voltages with (6X and 10X, respectively) and without a flattening filter (6XFFF and 10XFFF, respectively). FIG. 5 provides a visual example of the comparisons for a 6X beam and FIG. 6 provides a visual example of the comparisons for a 6XFFF beam.

Table 1 shows the results of the particle distribution comparisons for each beam configuration. Here, a p-value less than 0.05 indicates significant deviations between the two histograms.

Table 1. Comparison of VSM sampled particle parameters to phase-space file read particle parameters. Particle positions were compared at the phase-space surface (PSS) as well as at the treatment isocenter (ISO). Distributions over all sampled/read particles were compared using a $\chi^2$ test, p-values from which are shown for each parameter and beam configuration.

| Parameter | 6XFFF | 6X | 10XFFF | 10X |
|---|---|---|---|---|
| X (PSS) | 0.53 | 0.28 | 0.98 | 0.30 |
| X (ISO) | 0.86 | 0.41 | 0.98 | 0.61 |
| Y (PSS) | 0.44 | 0.41 | 0.98 | 0.42 |
| Y (ISO) | 0.95 | 0.98 | 0.98 | 0.71 |
| U | 0.40 | 0.89 | 0.26 | 0.42 |
| V | 0.29 | 0.30 | 0.79 | 0.68 |
| E | 0.89 | 0.62 | 0.14 | 0.40 |

In step 3700 treatment beams are simulated and transported using VSM through virtual treatment machines to the 3D CT densities according to radiotherapy plans to produce 3D images of simulated patient dose.

For each beam and control point, a number of particles are sampled from the VSM based on MU. Transport in the jaws and MLCs were modeled using first-order approximations following the Siebers-Keall method. Specifically, only attenuation and first Compton interactions are considered for primary photons and only attenuation is considered for scattered photons. A modified version of the PENELOPE Monte Carlo software to include a message-passing-interface (MPI) for parallel computation is used to transport particles through the patient CT volume and calculate dose delivered.

In step 3800 3D planned dose, organ segmentation contour, and simulated patient dose images are post-processed to obtain a final report comparing planned verses simulated dose.

The mean dose for regions corresponding to >80% of the maximum planned dose and the mead dose for a 1 cm³ region surrounding the point of maximum dose are calculated for the planned and simulated doses. A 3D gamma index analysis is performed to compare the planned and simulated doses. The gamma index is the minimum Euclidean distance in normalized dose-distance space:

$$\gamma(r_r) = \min\{\Gamma(r_r, r_e)\},$$

$$\Gamma(r_r, r_e) = |\hat{r}_r - \hat{r}_e| \forall \{r_e\},$$

$$\hat{r}_r = \left(\frac{r_r}{\Delta d}, \frac{D_r(r_r)}{\Delta D}\right),$$

$$\hat{r}_e = \left(\frac{r_e}{\Delta d}, \frac{D_r(r_e)}{\Delta D}\right).$$

Figure 7:
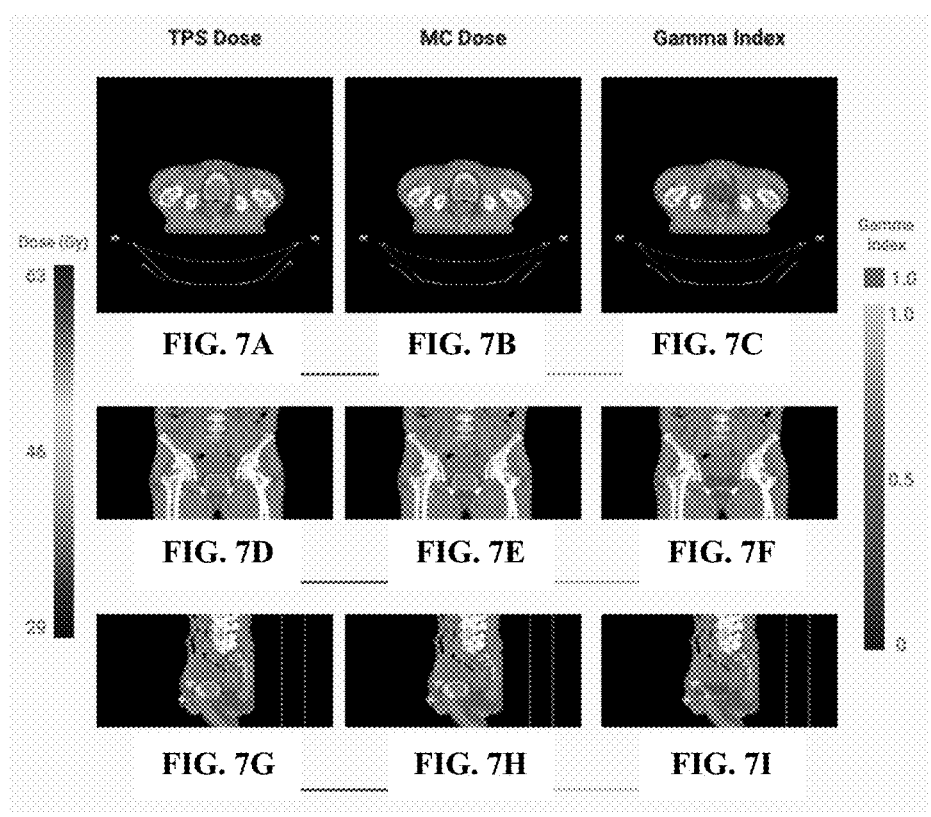
FIG. 7A shows an axial patient CT slice overlaid with the planned dose profile, according to an example of the present disclosure.
FIG. 7B shows an axial patient CT slice overlaid with the simulated dose profile, according to an example of the present disclosure.
FIG. 7C shows an axial patient CT slice overlaid with a gamma index map, according to an example of the present disclosure.
FIG. 7D shows a coronal patient CT slice overlaid with the planned dose profile, according to an example of the present disclosure.
FIG. 7E shows a coronal patient CT slice overlaid with the simulated dose profile, according to an example of the present disclosure.
FIG. 7F shows a coronal patient CT slice overlaid with a gamma index map, according to an example of the present disclosure.
FIG. 7G shows a sagittal patient CT slice overlaid with the planned dose profile, according to an example of the present disclosure.
FIG. 7H shows a sagittal patient CT slice overlaid with the simulated dose profile, according to an example of the present disclosure.
FIG. 7I shows a sagittal patient CT slice overlaid with a gamma index map, according to an example of the present disclosure.
Figure 8:
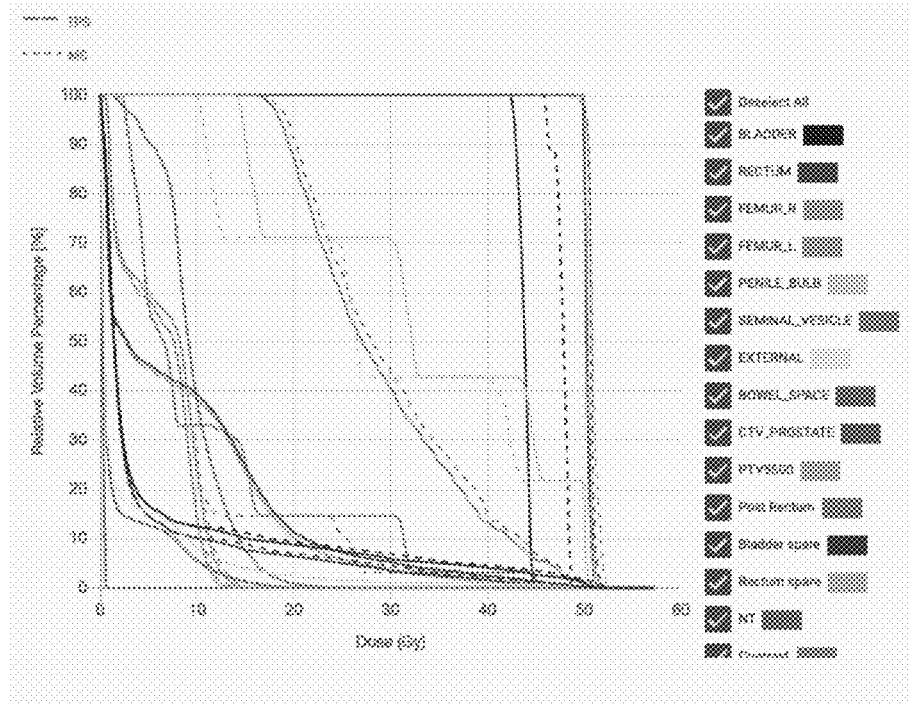
FIG. 8 shows dose volume histograms for multiple regions of interest for planned and simulated doses, according to an example of the present disclosure.

Here, $D_r(r_r)$ is the planned dose distribution at position $r_r$, $D_e(r_e)$ is the simulated dose at position $r_e$, and $\hat{r}_r$ and $\hat{r}_e$ are reference points from respective doses. User-specified dose difference and distance-to-agreement criteria are represented by $\Delta D$ and $\Delta d$, respectively. A gamma index value less than 1 indicates agreement between planned and simulated doses for a given voxel. The gamma index pass rate is the percentage of voxels that have a gamma index less than 1. FIG. 7 shows axial slices of planned dose, simulated dose and gamma index overlaid with patient CT. Dose volume histograms, which plot relative volume percentage verses dose for each region of interest are generated for planned and simulated dose. FIG. 8 shows an example DVH for the regions of interest from the CT in FIG. 7.

To validate the fast MC algorithm, radiotherapy cases were collected from the clinical practice at the University of Kentucky Department of Radiation Medicine. The cases used for testing comprise patients treated at University of Kentucky between 2015 and 2021 using a Varian→True-Beam Linac. Radiotherapy plan data sets were generated using the Eclipse V15.6 (Varian Medical System, Palo Alto, CA 94304) TPS. The imaging data sets for each patient were acquired using Computed Tomography Systems (GE Healthcare, Waukesha, Wisconsin) with 120 kV tube voltage and 2-3 mm slice reconstruction under an in-house imaging protocol. All data were anonymized to remove the protected health information of human subjects.

Five patient plans were selected for each beam configuration and were copied to a solid water phantom using a TPS for a total of 20 cases. The OCTAVIUS II (PTW, Frieburg, Germany) dose verification system was used. Patient plans were delivered to the water phantom and measurements of the 2D coronal dose distribution were obtained. The same patient plans and phantom CT images were exported to the fast MC algorithm for second check simulation using a 3% statistical uncertainty using the VSM. Two-dimensional slices corresponding to the coronal measurement plane from the MC calculation were exported to the MapCheck software (SunNuclear), which performed a 2D gamma analysis using 3%/3 mm criteria. In both studies, a gamma index passing rate above 90% for voxels receiving greater than 10% of the prescription dose was considered passing in the comparison between the MC and measured doses, which follows the clinical quality assurance procedures at the University of Kentucky.

Table 2 shows the results of the two-dimensional gamma index analysis (3%/3 mm) of the VSM MC and planned doses verses measured doses for water phantom plans.

TABLE 2

Two-dimensional gamma index analysis (3%/3 mm) of the virtual source model Monte Carlo (MC) and treatment planning system (TPS) doses verses measured doses for water phantom plans.

| Case | MC vs Measured $\gamma$ Rate (%) | TPS vs Measured $\gamma$ Rate (%) |
|---|---|---|
| Phantom 6X-1 | 99.2 | 100 |
| Phantom 6X-2 | 98.9 | 99.3 |
| Phantom 6X-3 | 99.6 | 99.6 |
| Phantom 6X-4 | 100.0 | 100.0 |
| Phantom 6X-5 | 99.3 | 99.9 |
| Phantom 6XFFF-1 | 99.3 | 98.9 |
| Phantom 6XFFF-2 | 100.0 | 100.0 |
| Phantom 6XFFF-3 | 97.5 | 99.5 |
| Phantom 6XFFF-4 | 99.3 | 97.9 |
| Phantom 6XFFF-5 | 98.8 | 98.3 |
| Phantom 10X-1 | 98.7 | 94.4 |
| Phantom 10X-2 | 99.6 | 99.6 |
| Phantom 10X-3 | 99.3 | 99.3 |
| Phantom 10X-4 | 100.0 | 100.0 |
| Phantom 10X-5 | 100.0 | 100.0 |
| Phantom 10XFFF-1 | 97.1 | 98.9 |
| Phantom 10XFFF-2 | 98.2 | 100.0 |
| Phantom 10XFFF-3 | 99.5 | 97.3 |
| Phantom 10XFFF-4 | 100.0 | 100.0 |
| Phantom 10XFFF-5 | 100.0 | 100.0 |

To validate the speed of the fast MC algorithm, five patient plans, from different patients from previous study, were selected for each beam configuration for a total of 20 test cases. Plans were exported to the fast MC algorithm for second check simulation using a 3% statistical uncertainty using both the PSF and VSM models. Virtual source model doses were compared against PSF doses through a 3D gamma analysis using 3%/3 mm criteria, which are common criteria used in clinical practice. Three dimensional gamma index passing rates were calculated using the "gamma" function from the python module PyMedPhys[34]. The computation time between the two MC methods was also assessed. Tests were run on a server with 64 GB of RAM and a 2.3 GHZ CPU. Files were read from an HDD with a buffered disk read rate of ≈250 MB/s and a cached memory read rate of ≈10,000 MB/s. The speed of PSF calculations is highly dependent on whether files were read from the disk or were cached from a previous simulation using the same PSF. Calculations for each case were run five times to determine the mean computation time for both cached and non-cached reads and illustrate best- and worst-case scenarios, respectively. The same number of threads (12) were used in parallel computations for both the VSM and PSF calculations. Completion times for each case using the VSM method were compared against raw and cached PSF completion times over all cases using paired t-tests. Here, a p-value less than 0.05 indicates a significant difference in the mean computation time between approaches (VSM vs raw PSF calculation time and VSM vs cached PSF calculation time).

Table 3 shows the comparison of the performance of the virtual source model (VSM) and phase-space file (PSF) implementations for Monte Carlo dose calculation in clinical cases

TABLE 3

Comparison of the performance of the virtual source model (VSM) and phase-space file (PSF) implementations for Monte Carlo dose calculation in clinical cases. Computation time is reported for both raw file reads as well as cached memory reads for the phase-space file implementation. Three-dimensional gamma index passing rates were calculated between the PSF- and VSM-generated Monte Carlo doses using 3%/3 mm criteria.

| Case | PSF Time (s) | PSF Cached Time (s) | VSM Time (s) | VSM vs PSF $\gamma$ Rate (%) |
|---|---|---|---|---|
| Clinical 6X-1 | 1879 | 70 | 136 | 99.1 |
| Clinical 6X-2 | 1740 | 54 | 115 | 98.9 |
| Clinical 6X-3 | 2114 | 69 | 133 | 94.9 |
| Clinical 6X-4 | 1882 | 85 | 155 | 98.9 |
| Clinical 6X-5 | 2166 | 59 | 121 | 90.8 |
| Clinical 6XFFF-1 | 1773 | 42 | 89 | 92.8 |
| Clinical 6XFFF-2 | 333 | 19 | 29 | 100.0 |
| Clinical 6XFFF-3 | 1589 | 55 | 105 | 96.6 |
| Clinical 6XFFF-4 | 1595 | 35 | 81 | 98.2 |
| Clinical 6XFFF-5 | 1738 | 41 | 86 | 95.9 |
| Clinical 10X-1 | 2140 | 124 | 197 | 97.8 |
| Clinical 10X-2 | 1564 | 40 | 100 | 93.7 |
| Clinical 10X-3 | 1664 | 46 | 107 | 96.1 |
| Clinical 10X-4 | 1621 | 114 | 190 | 96.3 |
| Clinical 10X-5 | 1499 | 78 | 145 | 94.3 |
| Clinical 10XFFF-1 | 1822 | 42 | 93 | 99.5 |
| Clinical 10XFFF-2 | 1682 | 180 | 248 | 99.7 |
| Clinical 10XFFF-3 | 1750 | 56 | 110 | 98.9 |
| Clinical 10XFFF-4 | 1700 | 96 | 155 | 97.7 |
| Clinical 10XFFF-5 | 906 | 34 | 83 | 93.3 |

Here, it is seen there is a dramatic decrease in computation time for the VSM compared to the raw PSF reads, which were on average ~14 times faster than the raw PSF reads, (Mean time difference $\Delta t=-1534$ s, $p<2.2\times10^{-16}$). Compared to cached memory reads of the PSF, the computation time of the VSM was ~1.9 times slower (Mean time difference $\Delta t=57$ s, $p<2.2\times10^{-16}$). This result is not unexpected, as in this situation, the overhead from repeatedly sampling particle parameters is competing with the immense speed of cached memory reads. Further, the fully cached scenario will be extremely improbable in practice, given the large PSF size and other processes sharing resources on the machine.

Extensive validation shows that the VSM sampling method, and the MC doses that arise from sampled particles, is robust and provides significant savings in both disk space usage and computation time without loss of quality results.

What is claimed is:

1. A computer-implemented method for fast MC dose calculation using a VSM and one or more processors, the method comprising:

receiving three-dimensional (3D) CT images obtained by a CT system;

receiving 3D planned dose images, 3D organ segmentation contour images, and radiotherapy plans generated by a treatment planning system (TPS);

processing 3D CT images, 3D planned dose images, 3D organ segmentation contour images to have the same spatial resolution and matrix size;

further processing 3D CT images to convert image intensity to 3D density maps;

processing the radiotherapy plans to generate instructions on how to simulate plan delivery;

building VSM using inverse cumulative density function (CDF) tables for the simulation of radiotherapy plans, wherein the step of building VSM comprises:

receiving output data files containing phase-space information for the radiation output of a specific medical linear accelerator treatment head;

calculating the probability of the inplane and crossplane positions of the radiation particles reverse transported from the phase-space surface back to the treatment head;

calculating the Gaussian means and standard deviations of the radiation particles' positions at the treatment head;

calculating the probabilities for the source of each radiation particle;

calculating the probabilities for the medical linear accelerator treatment head to produce different radiation particle species;

binning the inplane position probability information of radiation particles into a single histogram for each source and radiation particle species;

binning the crossplane position probability information of radiation particles into histograms for each bin of the inplane position histogram for each source and radiation particle species;

binning the inplane direction cosine probability information of radiation particles into histograms for each bin of the inplane position histogram for each source and radiation particle species;

binning the crossplane direction cosine probability information of radiation particles into histograms for each bin of the crossplane position histogram for each source and radiation particle species;

binning the kinetic energy probability information of radiation particles into radially binned histograms for each source and radiation particle species;

converting probability densities for inplane and crossplane positions, inplane and crossplane direction cosines, and kinetic energies histograms into cumulative probability densities for each source and radiation particle species; and inverting cumulative probability densities and converting into probability binned inverse CDF tables;

simulating and transporting external beams using VSM through virtual treatment machines to the 3D density maps according to radiotherapy plans to produce 3D simulated dose images; and post-processing the 3D planned dose images, 3D organ segmentation contour images, and the 3D simulated dose images to obtain a final report comparing planned versus simulated dose.

2. The computer-implemented method of claim 1, wherein processing 3D CT images, 3D planned dose images, 3D organ segmentation contour images to have the same spatial resolution and matrix size comprises:

receiving 3D images, 3D planned dose images, 3D organ segmentation contour images and their corresponding pixel spacing, slice thickness, and matrix size;

resizing the 3D CT images, 3D planned dose images, 3D organ segmentation contour images to have the same pixel spacing and matrix size; and applying lower and upper thresholds on the image intensities.

3. The computer-implemented method of claim 1, wherein further processing 3D CT images to convert image intensity to 3D density maps comprises:

receiving processed 3D CT images;

receiving intensity value to density table (IVDT); and applying IVDT to every voxel of the 3D CT images to convert CT intensity values to densities to obtain 3D density maps.

4. The computer-implemented method of claim 1, wherein processing the radiotherapy plans to generate instructions on how to simulate plan delivery comprises:

receiving radiotherapy plans and number of beams, energy modes per beam, total monitor units (MU) per beam, and control point information for each beam; and processing control point information to generate a list of instructions for radiotherapy plan simulation that includes control point MU, source axis distance, machine isocenter position, gantry rotation, couch rotation, collimator rotation, jaw positions, and MLC leaf positions.

5. The computer-implemented method of claim 1, wherein said output data files are obtained through Monte Carlo simulation of the primary electron interactions and radiation output of said specific medical linear accelerator treatment head.

6. The computer-implemented method of claim 1, wherein said radiation particle species includes photons, electrons, and positrons.

7. The computer-implemented method of claim 1, wherein the source of the radiation particles includes primary, particles that arise from Bremsstrahlung interactions in the treatment head, or scattered, particles that have been scattered by collimators or flattening filters.

8. The computer-implemented method of claim 1, wherein simulating and transporting external beams through virtual treatment machines to the 3D density map according to radiotherapy plans to produce 3D of simulated dose images comprises:

receiving 3D density maps, machine instructions, and VSM;

simulating treatment beams by sampling a number of particles, determined by control point MU;

using VSM to sample particle species, positions, direction cosines, and kinetic energies;

transporting simulated particles through the virtual machines by performing ray tracing with collimators, jaws, and MLC and determining if particles are scattered, attenuated, blocked, or pass unaffected;

transporting simulated particles that intersect with 3D density maps corresponding to patient volumes and calculating dose contribution per radiation particle; and summing up dose contributions from all radiation particles and control points and generating a 3D simulated dose images of the same size and volume as the input 3D density maps.

9. The computer-implemented method of claim 1, wherein post-processing 3D planned dose images, 3D organ segmentation contour images, and the simulated dose images to obtain a final report comparing planned versus simulated dose images comprises:

receiving 3D planned dose images, 3D organ segmentation contour images, and 3D simulated dose images;

calculating comparisons between 3D planned and 3D simulated dose images that include mean 3D dose comparisons, gamma index analyses, and dose volume histograms; and generating a report to summarize all comparisons.

10. An apparatus for fast MC dose calculation using a VSM, comprising:

one or more processors;

a display;

a non-transitory computer readable memory storing instructions executable by said one or more processors, wherein the instructions are configured to:

receive three-dimensional (3D) CT images obtained by a CT system;

receive 3D planned dose images, 3D organ segmentation contour images, and radiotherapy plans generated by a treatment planning system (TPS);

process 3D CT images, 3D planned dose images, 3D organ segmentation contour images to have the same spatial resolution and matrix size;

further process 3D CT images to convert image intensity to 3D density maps;

process the radiotherapy plans to generate instructions on how to simulate plan delivery;

build VSM using inverse cumulative density function (CDF) tables for the simulation of radiotherapy plans, wherein the step of building VSM includes instructions that are configured to:

receive output data files containing phase-space information for the radiation output of a specific medical linear accelerator treatment head;

calculate the probability of the inplane and crossplane positions of the radiation particles reverse transported from the phase-space surface back to the treatment head;

calculate the Gaussian means and standard deviations of the radiation particles' positions at the treatment head;

calculate the probabilities for the source of each radiation particle;

calculate the probabilities for the medical linear accelerator treatment head to produce different radiation particle species;

bin the inplane position probability information of radiation particles into a single histogram for each source and radiation particle species;

bin the crossplane position probability information of radiation particles into histograms for each bin of the inplane position histogram for each source and radiation particle species;

bin the inplane direction cosine probability information of radiation particles into histograms for each bin of the inplane position histogram for each source and radiation particle species;

bin the crossplane direction cosine probability information of radiation particles into histograms for each bin of the crossplane position histogram for each source and radiation particle species;

bin the kinetic energy probability information of radiation particles into radially binned histograms for each source and radiation particle species;

convert probability densities for inplane and crossplane positions, inplane and crossplane direction cosines, and kinetic energies histograms into cumulative probability densities for each source and radiation particle species; and invert cumulative probability densities and converting into probability binned inverse CDF tables;

simulate and transport external beams using VSM through virtual treatment machines to the 3D density maps according to radiotherapy plans to produce 3D simulated dose images; and post-process the 3D planned dose images, 3D organ segmentation contour images, and the 3D simulated dose images to obtain a final report comparing planned versus simulated dose.

11. The apparatus for fast MC dose calculation using a VSM, according to claim 10, processing the 3D CT images, 3D planned dose images, 3D organ segmentation contour images to have the same spatial resolution and matrix size comprises:

receiving 3D CT images, 3D planned dose images, 3D organ segmentation contour images and their corresponding pixel spacing, slice thickness, and matrix size;

resizing the 3D CT images, 3D planned dose images, 3D organ segmentation contour images to have the same pixel spacing and matrix size; and applying lower and upper thresholds on the image intensities.

12. The apparatus for fast MC dose calculation using a VSM, according to claim 10, wherein further processing 3D CT images to convert image intensity to 3D density maps comprises:

receiving processed 3D CT images;

receiving intensity value to density table (IVDT); and applying IVDT to every voxel of the 3D CT images to convert CT intensity values to densities to obtain 3D density maps.

13. The apparatus for fast MC dose calculation using a VSM, according to claim 10, wherein processing the radiotherapy plans to generate instructions on how to simulate plan delivery comprises:

receiving radiotherapy plans and number of beams, energy modes per beam, total monitor units (MU) per beam, and control point information for each beam; and processing control point information to generate a list of instructions for radiotherapy plan simulation that includes control point MU, source axis distance, machine isocenter position, gantry rotation, couch rotation, collimator rotation, jaw positions, and MLC leaf positions.

14. The apparatus for fast MC dose calculation using a VSM, according to claim 10, wherein said output data files are obtained through Monte Carlo simulation of the primary electron interactions and radiation output of said specific medical linear accelerator treatment head.

15. The apparatus for fast MC dose calculation using a VSM, according to claim 10, wherein said radiation particle species includes photons, electrons, and positrons.

16. The apparatus for fast MC dose calculation using a VSM, according to claim 10, wherein the source of the radiation particles includes primary, particles that arise from Bremsstrahlung interactions in the treatment head, or scattered, particles that have been scattered by collimators or flattening filters.

17. The apparatus for fast MC dose calculation using a VSM, according to claim 10, wherein simulating and transporting external beams through virtual treatment machines to the 3D densities map according to radiotherapy plans to produce 3D simulated dose images comprises:

receiving 3D density maps, machine instructions, and VSM;

simulating treatment beams by sampling a number of particles, determined by control point MU;

using VSM to sample particle species, positions, direction cosines, and kinetic energies;

transporting simulated particles through the virtual machines by performing ray tracing with collimators, jaws, and MLC and determining if particles are scattered, attenuated, blocked, or pass unaffected;

transporting simulated particles that intersect with 3D density maps corresponding to patient volumes and calculating dose contribution per radiation particle; and summing up dose contributions from all radiation particles and control points and generating a 3D simulated dose images of the same size and volume as the input 3D density maps.

18. The apparatus for fast MC dose calculation using a VSM, according to claim 10, wherein post-processing 3D planned dose, 3D organ segmentation contour images, and the 3D simulated dose images to obtain a final report comparing planned versus simulated dose comprises:

receiving 3D planned dose images, 3D organ segmentation contour images, and 3D simulated dose images;

calculating comparisons between 3D planned and 3D simulated dose images that include mean 3D dose comparisons, gamma index analyses, and dose volume histograms; and generating a report to summarize all comparisons.

19. A non-transitory computer-readable storage medium having stored therein instructions that, when executed by one or more processors of an apparatus causing the apparatus to perform acts comprising:

receiving three-dimensional (3D) CT images obtained by a CT system;

receiving 3D planned dose images, 3D organ segmentation contour images, and radiotherapy plans generated by a treatment planning system (TPS);

processing 3D CT images, 3D planned dose images, 3D organ segmentation contour images to have the same spatial resolution and matrix size;

further processing 3D CT images to convert image intensity to 3D density maps;

processing radiotherapy plans to generate instructions on how to simulate plan delivery;

building VSM using inverse cumulative density function (CDF) tables for the simulation of radiotherapy plans, wherein the step of building VSM comprises:

receiving output data files containing phase-space information for the radiation output of a specific medical linear accelerator treatment head;

calculating the probability of the inplane and crossplane positions of the radiation particles reverse transported from the phase-space surface back to the treatment head;

calculating the Gaussian means and standard deviations of the radiation particles' positions at the treatment head;

calculating the probabilities for the source of each radiation particle;

calculating the probabilities for the medical linear accelerator treatment head to produce different radiation particle species;

binning the inplane position probability information of radiation particles into a single histogram for each source and radiation particle species;

binning the crossplane position probability information of radiation particles into histograms for each bin of the inplane position histogram for each source and radiation particle species;

binning the inplane direction cosine probability information of radiation particles into histograms for each bin of the inplane position histogram for each source and radiation particle species;

binning the crossplane direction cosine probability information of radiation particles into histograms for each bin of the crossplane position histogram for each source and radiation particle species;

binning the kinetic energy probability information of radiation particles into radially binned histograms for each source and radiation particle species;

converting probability densities for inplane and crossplane positions, inplane and crossplane direction cosines, and kinetic energies histograms into cumulative probability densities for each source and radiation particle species; and inverting cumulative probability densities and converting into probability binned inverse CDF tables;

simulating and transporting external beams using VSM through virtual treatment machines to the 3D density maps according to radiotherapy plans to produce 3D simulated dose images; and post-processing the 3D planned dose images, 3D organ segmentation contour images, and the 3D simulated dose images to obtain a final report comparing planned versus simulated dose.

* * * * *